United States Patent [19]

Reale, Jr.

[11] Patent Number: 5,032,278

[45] Date of Patent: Jul. 16, 1991

[54] PROCESS FOR DEHYDRATION OF ORGANIC OXYGENATES

[75] Inventor: John Reale, Jr., Wappingers Falls, N.Y.

[73] Assignee: Texaco Inc., White Plains, N.Y.

[21] Appl. No.: 563,017

[22] Filed: Aug. 6, 1990

[51] Int. Cl.$^5$ .................. B01D 61/36; B01D 69/00
[52] U.S. Cl. ........................ 210/640; 210/654
[58] Field of Search .......... 210/640, 500.39, 644, 210/649–654

[56] References Cited

U.S. PATENT DOCUMENTS 4,808,313  2/1989  Michizuki et al. ............... 210/640
4,865,745  9/1989  Pasternak ....................... 210/500.39

*Primary Examiner*—Frank Sever
*Attorney, Agent, or Firm*—Robert A. Kulason; James J. O'Loughlin; Carl G. Seutter

[57] ABSTRACT

A polyethylenimine membrane which has been crosslinked by heat treating at 100° C.–200° C. for 3–20 minutes may be used to dewater isopropanol or methyl ethyl ketone/toluene mixtures.

12 Claims, No Drawings

PROCESS FOR DEHYDRATION OF ORGANIC OXYGENATES

FIELD OF THE INVENTION

This invention relates to the dehydration of organic oxygenates such as isopropyl alcohol. More particularly it relates to a membrane technique for effecting separation of water from an aqueous mixture containing isopropyl alcohol.

BACKGROUND OF THE INVENTION

As well known to those skilled in the art, it is possible to remove water from mixtures thereof with organic liquids by various techniques including adsorption or distillation. These conventional processes, particularly distillation, are however, characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs: principally costs of heating and cooling—plus pumping, etc.

Furthermore the properties of the materials being separated, as is evidenced by the distillation curves, may be such that a large number of plates may be required, etc. when the material forms an azeotrope with water, additional problems may be present which, for example, would require that separation be effected in a series of steps (e.g., as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the saturated vapor pressure of the permeating species.

Illustrative membranes which have been employed in prior art techniques include those set forth in the following table:

TABLE

| Separating Layer | References |
| --- | --- |
| Nafion brand of perfluorosulfonic acid | Cabasso and Liu J. Memb. Sci. 24, 101 (1985) |
| Sulfonated polyethylene | Cabasso, Korngold & Liu J. Pol. Sci Letters, 23, (1985) |
| Fluorinated polyether or Carboxylic Acid fluorides | U.S. Pat. No. 4,526,948 to Dupont as assignee of Resnick |
| Selemion AMV brand of Asahi Glass cross-linked styrene butadiene (with quaternary ammonium residues on a polyvinyl chloride backing) | Wentzlaff Boddeker & Hattanback, J. Memb. Sci. 22, 333 (1985) |
| Cellulose triacetate | Wentzlaff, Boddeker & Hattanback, J. Memb. Sci. 22, 333 (1985) |
| Polyacrylonitrile | Neel, Aptel & Clement Desalination 53, 297 (1985) |
| Crosslinked Polyvinyl Alcohol | Eur. Patent 0 096 339 to GFT as assignee of Bruschke |
| Poly(maleimideacrylonitrile) | Yoshikawa et al J. Pol. Sci. 22, 2159 (1984) |
| Dextrine-isophorone-diisocyanate | Chem. Econ. Eng. Rev., 17, 34 (1985) |

The cost effectiveness of a membrane is determined by the selectivity and productivity. Of the membranes commercially available, an illustrative membrane of high performance is that disclosed in European Patent 0 096 339 A2 of GFT as assignee of Bruschke—published 21Dec. 1983.

European Patent 0 096 339 A2 to GFT as assignee of Bruschke discloses, as cross-linking agents for the polyvinyl alcohol membrane, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically, the composite includes (i) a backing typically about 120 microns in thickness, on which is positioned (ii) a microporous support layer of a polysulfone or a polyacrylonitrile of about 50 microns thickness, on which is positioned (iii) a separating layer of cross-linked polyvinyl alcohol about 2 microns in thickness.

USP 4,728,429 to Cabasso et al, USP 4,067,805 to Chiang et al, USP 4,526,948 to Resnick, USP 3,750,735 to Chiang et al, USP 4,690,766 to Linder et al, and USP 4,798,674 to Pasternak, Bartels and Reale, Jr. provide additional background. See also Yamamoto et al Japanese 61/161109 A2 of 21 July 1986 *Preparation of Separation Membranes*.

It is an object of this invention to provide a novel composite membrane characterized by its ability to effect separation of water from organic oxygenates such as isopropyl alcohol. Other objects will be apparent to those skilled in the art.

STATEMENT OF THE INVENTION

In accordance with certain of its aspects, this invention is directed to a method of concentrating a charge aqueous mixture containing an organic oxygenate which comprises maintaining a non-porous separating layer of polyimine membrane which has been thermally cross-linked;

maintaining a pressure drop across said non-porous polyimine separating layer;

passing a charge aqueous mixture containing an organic oxygenate into contact with the high pressure side of said non-porous polyimine separating layer whereby at least a portion of said water in said charge aqueous mixture and a lesser portion of organic oxygenate in said charge aqueous mixture pass by pervaporation through said non-porous polyimine separating layer as a lean mixture containing more water and less organic oxygenate than are present in said charge aqueous mixture and said charge aqueous solution is converted to a rich liquid containing less water and more organic oxygenate than are present in said charge aqueous mixture;

recovering from the low pressure side of said non-porous polyimine separating layer said lean mixture containing more water and less organic oxygenate than are present in said charge aqueous mixture, said lean mixture being recovered in vapor phase at a pressure below the vapor pressure thereof; and recovering from the high pressure side of said nonporous polyimine separating layer said rich liquid containing a lower water content and a higher organic oxygenate content than are present in said charge aqueous mixture.

In accordance with certain of its other aspects, this invention is directed to a non-porous separating layer of thickness of 0.2–10.0 microns of polyimine membrane of molecular weight $\overline{M}_n$ of 40,000–100,000 which has been thermally cross-linked.

DESCRIPTION OF THE INVENTION

The composite structure of this invention includes a multi-layer assembly which in the preferred embodiment preferably includes a porous carrier layer which provides mechanical strength and support to the assembly.

THE CARRIER LAYER

This carrier layer, when used, is characterized by its high degree of porosity and mechanical strength. It may be fibrous or non-fibrous, woven or non-woven. In the preferred embodiment, the carrier layer may be a porous, flexible, non-woven fibrous polyester.

A preferred non-woven polyester carrier layer may be formulated of non-woven, thermally-bonded strands and characterized by a fabric weight of 80±8 grams per square yard, a thickness of 4.2±0.5 mils, a tensile strength (in the machine direction) of 31psi and (in cross direction) of 10 psi, and a Frazier air permeability of 6 cuft/min/sq. ft. @ 0.5 inches of water.

THE POROUS SUPPORT LAYER

The porous support layer of this invention is preferably formed of a sheet of polysulfone polymer or more preferably of polyacrylonitrile. Typically, the polysulfone may be of thickness of 40–80 microns, say 50 microns and of molecular weight $\overline{M}_n$ of 5,000–100,000, preferably 20,000–60,000 say 40,000. The polysulfone is preferably characterized by a pore size of less than about 500A and typically about 200A. This corresponds to a molecular weight cut-off of less than about 25,000 typically about 20,000.

The sulfone polymers which may be employed may include those made from cumene containing isopropylidene groups in the backbone; e.g.

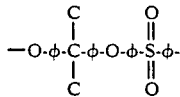

These isopropylidene sulfones containing repeating units including ether-aromatic-isopropylidene-aromatic-ether-aromatic-sulfone-aromatic groups may typically have a molecular weight $\overline{M}_n$ of 15,000–30,000, a water absorption (at 20° C.) of about 0.85 w %, a glass transition temperature of 449° K., a density of 1.25 mg/m³, a tensile strength (at 20° C.) at yield of 10,000 psi, and a coefficient of linear thermal expansion of $2.6 \times 10^{-5}$ mm/mm/°C.

It is found, however, that when the sulfone polymers are employed in practice of the process of this invention, it is preferred to use those which are free of isopropylidene moieties in the backbone chain and wherein the phenylene group in the backbone are bonded only to ether oxygen atoms and to sulfur atoms. These preferred sulfone polymers, which may be typically prepared from

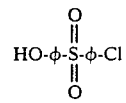

may be characterized by a backbone containing the following repeating group:

A preferred sulfone polymer may be a polyether sulfone which is free of isopropylidene moieties in the backbone chain and wherein the phenylene groups in the backbone are bonded only to ether-oxygen atoms and to sulfur atoms. This polymer may be characterized by molecular weight $M_n$ of 25,000, water absorption @ 20° C. of 2.1 w %, glass transition temperature of 487° K., tensile strength at yield of 12,200 psig at 20° C.; and coefficient of linear thermal expansion of $5.5 \times 10^{-5}$ mm/mm/° C. This polymer has a molecular weight cut off of about 20,000 and has a pore size of about 200A.

It is, however, preferred to use, as the porous support layer, a polyacrylonitrile polymer typically having a molecular weight cut off of about 40,000.

THE SEPARATING LAYER

The separating layer which permits attainment of separation in accordance with the process of this invention includes a non-porous film or membrane of 0.2–10.0 microns, say about 3.0 microns of a polyimine polymer of molecular weight $M_n$ of about 40,000–100,000, say about 60,000 (prior to cross-linking), which is thermally cross-linked.

Polyimine polymers are characterized by the presence of recurring —N—R"— groups as integral parts of the main polymer chain. Typical structural formula of linear polyimines may be represented as $$H_2N-R''[N-R'']_n-NH_2$$

wherein n represents the degree of polymerization or number of recurring groups in the polymer chain.

In the above formula, R" may preferably be a hydrocarbon group selected from the group consisting of alkylene, aralkylene, cycloalkylene, arylene, and alkarylene, including such radicals when inertly substituted. When R" is alkylene, it may typically be methylene, ethylene, n-propylene, iso-propylene, n-butylene, i-butylene, sec-butylene, amylene, octylene, decylene, octadecylene, etc. When R" is aralkylene, it may typically be benzylene, beta-phenylethylene, etc. When R" is cycloalkylene, it may typically be cyclohexylene, cycloheptylene, cyclooctylene, 2-methylcycloheptylene, 3-butylcyclohexylene, 3-methylcyclohexylene, etc. When R" is arylene, it may typically be phenylene, naphthylene, etc. When R is alkarylene, it may typically be tolylene, xylylene, etc. R" may be inertly substituted i.e. it may bear a non-reactive substituent such as alkyl, aryl, cycloalkyl, ether, etc. typically inertly substituted R" groups may include 3-methoxypropylene, 2-ethoxyethylene, carboethoxymethylene, 4-methylcyclohexylene, p-methylphenylene, p-methylbenzylene, 3-ethyl-5-methylphenylene, etc. The preferred R" groups may be phenylene or lower alkylene, i.e. $C_1$–$C_{10}$ alkylene, groups including e.g. methylene, ethylene, n-propylene, i-propylene, butylene, amylene, hexylene, octylene, decylene, etc. R" may preferably be phenylene or ethylene —$CH_2CH_2$—.

Illustrative polyimine polymers include those of molecular weight $\overline{M}_n$ of 40,000–100,000, say 60,000.

Suitable polyimines may include the following, the first listed being preferred:

TABLE

A. Virginia Chemical Company Corcat P-600 brand of polyethylenimine ($\overline{M}_n$ of 60,000) in 33 w % aqueous solution–Brookfield viscosity @ 25° C. of 5000 cP, Sp.Gr & 25° C. of 1.04–1.06, and pH of 10–11, having the formula

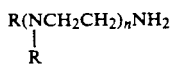

wherein R is H or $(CH_2CH_2N)_x$ (containing 30% primary, 40% secondary, and 30% tertiary amines).

B. Dow Chemical Co Tydex 12 brand of polyethylenimine ($\overline{M}_n$ of 50,000) in 30 w % aqueous solution having the same formula as the Corcat P-600 membrane.

The separating layer may be formed on the porous support layer (preferably mounted on the carrier layer) as by coating with a 5–20 w %, say 15 w % solution of the polyimine in water/isopropanol solvent. Preferred solvent may include 0–100 w %, say 15w % isopropanol.

Thermal cross-linking of the polyimine membrane may be effected by heating the membrane to 100° C.–200° C., typically 120° C.–140° C., say 125° C. for 3–20 minutes, typically 5–15 minutes, say 10 minutes.

THE COMPOSITE MEMBRANE

It is a feature of this invention that it may utilize a composite membrane which comprises (i) a carrier layer characterized by mechanical strength, for supporting a porous support layer and a separating layer (ii) a porous support layer such as a polyacrylonitrile membrane of 40–80 microns, and of molecular weight cut off of 25,000–100,000, and (iii) as a non-porous separating layer a polyimine of molecular weight $\overline{M}_n$ of 40,000–100,000, which has been thermally cross-linked.

It is possible to utilize a spiral wound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There is then placed on one face of the bag-like unit, adjacent to the separating layer and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the perforations of the conduit; and the bag-like unit is wrapped around the conduit to form a spiral wound configuration. It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit. The unit is fitted within a shell (in manner comparable to a shell-and-tube heat exchanger) provided with an inlet at one end and an outlet at the other. A baffle-like seal between the inner surface of the shell and the outer surface of the spiral-wound unit prevents fluid from bypassing the operative membrane system and insures that fluid enters the system principally at one end. The charge passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The liquid which permeates the membrane passes into the volume occupied by the permeate spacer and through this permeate channel to the perforations in the cylindrical conduit through which it is withdrawn from the system.

In another embodiment, it is possible to utilize the system of this invention as a tubular or hollow fibre. In this embodiment, the polyacrylonitrile porous support layer may be extruded as a fine tube with a wall thickness of typically 0.0001–0.1 mm. The extruded tubes are passed through a bath of polyethyleneimine which is cross-linked and cured in situ. A bundle of these tubes is secured (with an epoxy adhesive) at each end in a header; and the fibers are cut so that they are flush with the ends of the header. This tube bundle is mounted within a shell in a typical shell-and-tube assembly.

In operation, the charge liquid is admitted to the shell side and passes around the tubes and exits as retentate. During passage, permeate passes through the non-porous separating layer and permeate is collected in the tube side.

PERVAPORATION

It is a feature of the non-porous polyimine separating layer that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 5 mm. Hg.

For general background on pervaporation, note U.S. Pat. No. 4,277,344; U.S. Pat. No. 4,039,440; U.S. Pat. No. 3,926,798; U.S. Pat. No. 3,950,247; U.S. Pat. No. 4,035,291; etc.

It is a feature of the process of this invention that the novel membrane may be particularly useful in pervaporation processes for dewatering aqueous mixtures of organic oxygenates. It may be possible to utilize the process of this invention to remove water from immiscible mixtures therewith as in the case of ethyl acetate (solubility in water at 15° C. of 8.5 parts per 100 parts of water). It will be apparent to those skilled in the art that it may be desirable to separate large quantities of water from partially miscible systems as by decantation prior to utilizing the process of the invention to remove the last traces of water.

The advantages of the instant invention are more apparent when the charge liquid is a single phase homogeneous aqueous solution as is the case for example with isopropanol. The system may also find use in the case of slightly soluble liquids wherein two phases are present (i) water-oxygenate first phase and, as a second phase (ii) either water or oxygenate. Clearly those charge liquids which contain only a small portion of an immiscible second liquid phase may benefit most from the process of this invention. It is also a feature of this invention that it may be particularly useful to separate azeotropes such as isopropanol-water.

The charge organic oxygenates which may be treated by the process of this invention may include alcohols, glycols, acids, esters, ketones, aldehydes, etc. It will be apparent to those skilled in the art that the charge organic oxygenates used should be inert with respect to the separating membrane. Clearly a system wherein the membrane is attacked by the components of the charge liquid will not yield significant separation for any reasonable period of time. Best results may be achieved when treating alcohols (such as isopropanol) or ketones (such as methyl ethyl ketone). Results achieved with acids are generally less satisfactory.

Illustrative alcohols may include ethanol, propanol, n-butanol, i-butanol, t-butanol, amyl alcohols, hexyl alcohols, etc.

Illustrative glycols may include ethylene glycol, propylene glycols, butylene glycol or glycol ethers such as diethylene glycol, triethylene glycol, or triols, including glycerine, etc.

Illustrative acids may include formic acid, oxalic acid, acetic acid, propionic acid, etc.

Illustrative esters may include ethyl acetate, methyl acetate, butyl acetate, methyl benzoate, ethylene glycol mono acetate, propylene glycol monostearate, etc.

Illustrative ethers may include tetrahydrofoian, diethyl ether, and diisopropyl ether.

Illustrative ketones may include acetone, methyl ethyl ketone, acetophenone, etc.

Illustrative aldehydes may include formaldehyde, acetaldehyde, propionaldehyde, etc.

It is believed that the advantages of this invention are most apparent where the organic oxygenate is a liquid which is infinitely miscible with water—typified by isopropyl alcohol.

A typical charge may be an aqueous solution containing 70%–95%, say 80 w % isopropanol.

In practice of the pervaporation process of this invention, the charge aqueous organic oxygenate solution typically at 40° C.–120° C., say 80° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 2–50 preferably 5–20, say 10 mm. Hg.

The permeate which passes through the membrane includes water and a small proportion of the organic oxygenate from the charge liquid. Typically, the permeate contains 80–99.0, say 99 w % water. Permeate is recovered in vapor phase.

Pervaporation may typically be carried out at a flux of 0.01–10, say 1.9 gallons per square foot per day which corresponds to about 0.17–16.9, say 3.2 kilograms per square meter per hour (kmh). Typically, the units may show good separation (measured in terms of w % organic oxygenate in the permeate during pervaporation of an aqueous solution of organic oxygenate through a polyimine separating layer.

Practice of the process of this invention will be apparent to those skilled in the art from inspection of the following examples wherein, as elsewhere in this specification, all parts are parts by weight unless otherwise stated. An asterisk indicates a control example.

DESCRIPTION OF SPECIFIC EMBODIMENTS

Practice of the process of this invention may be apparent to those skilled in the art from the following examples wherein, as elsewhere in this specification, all parts are parts by weight unless otherwise stated. An asterisk (*) indicates a control example.

EXAMPLE I

In this example which represents the best mode of carrying out the process of this invention, the carrier layer is the woven polyester backing described supra. The porous support layer is the commercially available layer of Daicel DUY-L polyacrylonitrile of molecular weight cut off of 40,000.

The polyethyleneimine PEI separating layer is fabricated from the Corcat P-600 brand of polyethyleneimine of the Table supra ($\overline{M}_n$ of 60,000). This 33 w % aqueous solution is diluted to 15.0 w % by addition of IPA/water. This solution is deposited on the porous support layer and is then thermally cross-linked.

The assembly containing the preferred microporous polyacrylonitrile supra as porous support layer and the woven polyester backing supra as carrier layer (total area Ca 45 cm$^2$) is contacted with the dilute aqueous solution of polyethyleneimine.

The assembly is then thermally cross-linked in an oven at 125° C. for 5 minutes.

The membrane is mounted in a standard cell. There is admitted to the cell and to the non-porous polyethyleneimine separating layer a charge liquid containing methyl ethyl ketone and toluene in 2:1 weight ratio plus 3.0 w % water—at 70° C.

Separation is carried out at 70° C. and a permeate pressure is 55 mm Hg. Selectivity is measured and reported as % water in permeate. Clearly a higher selectivity is desired, as this means that the retentate desirably contains less water and the permeate desirably contains more water. Flux is measured as kilograms per square meter per hour (kmh).

In this Example, the Selectivity is 98.5% water and the Flux is 3.2 kmh.

EXAMPLES II–IV

In this series of Examples, the procedure of Example I is duplicated, except that the time of thermal cross-linking is 7, 9 and 10 minutes in Examples II, III and IV, respectively.

TABLE

| Example | Time | Permeate Conc. w % Water | Flux (kmh) |
| --- | --- | --- | --- |
| I | 5 | 98.5 | 3.2 |
| II | 7 | 94.3 | 1.4 |
| III | 9 | 98.1 | 2.1 |
| IV | 10 | 97.8 | 2.2 |

EXAMPLES V-VIII

In this series of Examples, the charge liquid contains 14.4 w % water and 85.6 w % isopropanol at 70° C.

TABLE

| Example | Time | Permeate Conc. w % Water | Flux (kmh) |
| --- | --- | --- | --- |
| V | 5 | 76.1 | 3.5 |
| VI | 7 | 91.0 | 3.6 |
| VII | 9 | 96.8 | 3.1 |
| VIII | 10 | 97.5 | 2.8 |

Results comparable to the above may be attained if the charge is

TABLE

| Example | Charge |
| --- | --- |
| IX | 95 w % ethanol |
|  | 5 w % water |
| X | 80% ethylene glycol |
|  | 20% water |
| XI | 70% acetic acid |
|  | 30% water |
| XII | 70% ethyl acetate |
|  | 30% water |
| XIII | 90% methyl isobutyl ketone |
|  | 10% water |
| XIV |  |

Although this invention has been illustrated by reference to specific embodiments, it will be apparent to those skilled in the art that various changes and modifications may be made which clearly fall within the scope of the invention.

What is claimed is:

1. The method of concentrating a charge aqueous mixture containing an organic oxygenate which comprises:

maintaining a non-porous separating layer of polyimine membrane which has been thermally cross-linked;

maintaining a pressure drop across said non-porous polyimine separating layer;

passing a charge aqueous mixture containing an organic oxygenate into contact with the high pressure side of said non-porous polyimine separating layer whereby at least a portion of said water in said charge aqueous mixture and a lesser portion of organic oxygenate in said charge aqueous mixture pass by pervaporation through said non-porous polyimine separating layer as a lean mixture containing more water and less organic oxygenate than are present in said charge aqueous mixture and said charge aqueous mixture is converted to a rich liquid containing less water and more organic oxygenate than are present in said charge aqueous mixture;

recovering from the low pressure side of said non-porous polyimine separating layer, said lean mixture containing more water and less organic oxygenate than are present in said charge aqueous mixture, said lean mixture being recovered in vapor phase at a pressure below the vapor pressure thereof; and recovering from the high pressure side of said non-porous separating layer said rich liquid containing a lower water content and a higher organic oxygenate content than are present in said charge aqueous mixture.

2. The method of concentrating a charge aqueous composition as claimed in claim 1 wherein said polyimine is polyethyleneimine.

3. The method of concentrating a charge aqueous composition as claimed in claim 1 wherein thermal cross-linking is carried out at 100° C.–200° C.

4. The method of concentrating a charge aqueous composition as claimed in claim 1 wherein thermal cross-linking is carried out for 3–20 minutes.

5. The method of concentrating a charge aqueous composition as claimed in claim 1 wherein said charge aqueous composition contains a ketone.

6. The method of concentrating a charge aqueous composition as claimed in claim 1 wherein said charge aqueous composition contains methyl ethyl ketone.

7. The method of concentrating a charge aqueous composition as claimed in claim 1 wherein said charge aqueous composition contains methyl isobutyl ketone.

8. The method of concentrating a charge aqueous composition as claimed in claim 1 wherein said charge aqueous composition contains a ketone and toluene.

9. The method of concentrating a charge aqueous composition as claimed in claim 1 wherein said charge aqueous composition contains an alcohol.

10. The method of concentrating a charge aqueous composition as claimed in claim 1 wherein said charge aqueous composition contains isopropanol.

11. The method of concentrating a charge aqueous mixture containing methyl ethyl ketone and toluene which comprises:

maintaining a non-porous separating membrane layer of polyethylene imine membrane which has been thermally cross-linked at 100° C.–200° C. for 3–20 minutes;

maintaining a pressure drop across said non-porous separating membrane layer;

passing a charge aqueous mixture containing methyl ethyl ketone and toluene into contact with the high pressure side of said non-porous polyethylene imine separating layer whereby at least a portion of said water in said charge aqueous mixture pass by pervaporation through said non-porous polyethylene separating layer as lean mixture containing more water and less methyl ethyl ketone and toluene than are present in said charge aqueous mixture and said charge aqueous mixture is converted to a rich liquid containing less water and more methyl ethyl ketone and toluene than are present in said charge aqueous mixture;

recovery from the low pressure side of said non-porous polyethylene imine separating layer, said lean mixture containing more water and less methyl ethyl ketone and toluene than are present in said charge aqueous mixture, said lean mixture being recovered in vapor phase at a pressure below the vapor pressure thereof; and recovery from the high pressure side of said non-porous separating layer said rich liquid containing a lower water content and a higher methyl ethyl ketone and toluene content than are present in said charge aqueous mixture.

12. The method of concentrating a charge aqueous mixture containing ethanol which comprises:

maintaining a non-porous separating layer of polyimine membrane which has been thermally cross-linked;

maintaining a pressure drop across said non-porous polyimine separating layer;

passing a charge aqueous mixture containing ethanol into contact with the high pressure side of said non-porous polyimine separating layer whereby at least a portion of said water in said charge aqueous mixture and a lesser portion of ethanol in said charge aqueous mixture pass by pervaporation through said non-porous polyimine separating layer as a lean mixture containing more water and less ethanol than are present in said charge aqueous mixture and said charge aqueous mixture is converted to a rich liquid containing less water and more ethanol than are present in said charge aqueous mixture;

recovering from the low pressure side of said non-porous polyimine separating layer, said lean mixture containing more water and less ethanol than are present in said charge aqueous mixture, said lean mixture being recovered in vapor phase at a pressure below the vapor pressure thereof; and recovering from the high pressure side of said non-porous separating layer said rich liquid containing a lower water content and a higher ethanol content than are present in said charge aqueous mixture.

* * * * *